United States Patent [19]

Ferrari et al.

[11] 4,017,603
[45] Apr. 12, 1977

[54] WATER-SOLUBLE PHARMACEUTICAL COMPLEXES OF PARTRICIN OR AN ALKYL ESTER THEREOF WITH SODIUM DESOXYCHOLATE OR SODIUM DEHYDROCHOLATE

[75] Inventors: Rodolfo Ferrari; Ernani Dell'Acqua, both of Milan, Italy

[73] Assignee: SPA-Societa Prodotti Antibiotici S.p.A., Milan, Italy

[22] Filed: Aug. 29, 1975

[21] Appl. No.: 609,143

[30] Foreign Application Priority Data

Sept. 3, 1974    United Kingdom ............ 38412/74

[52] U.S. Cl. ................................................ 424/122
[51] Int. Cl.² ........................................ A61K 35/00
[58] Field of Search .................................... 424/122

[56] References Cited

UNITED STATES PATENTS 3,773,925  11/1973  Bruzzese et al. .................. 424/122
3,780,173  12/1973  Bruzzese et al. .................. 424/122

*Primary Examiner*—Albert T. Meyers
*Assistant Examiner*—Daren M. Stephens
*Attorney, Agent, or Firm*—Wenderoth, Lind & Ponack

[57]    ABSTRACT

The present invention provides a water-soluble pharmaceutical complex, comprising the antibiotic partricin and/or an alkyl ester thereof and sodium desoxycholate and/or sodium dehydrocholate.

4 Claims, No Drawings

WATER-SOLUBLE PHARMACEUTICAL COMPLEXES OF PARTRICIN OR AN ALKYL ESTER THEREOF WITH SODIUM DESOXYCHOLATE OR SODIUM DEHYDROCHOLATE

BACKGROUND OF THE INVENTION

In U.S. Pat. No. 3,773,925, there is described and claimed the new antibiotic partricin, in U.S. Pat. No. 3,780,173, there is described and claimed the methyl ester of partricin and in co-pending U.S. patent application Ser. No. 441,988 dated Feb. 13, 1974, there are described and claimed certain alkyl esters of partricin other than its methyl ester.

Although partricin and its alkyl esters have good solubilities in some organic solvents, they are practically insoluble in water, which is a disadvantage since water is the preferred medium for administering drugs by injection.

As a result of our investigations, we found that partricin and its methyl ester form water-soluble complexes with certain surfactants. In co-pending U.S. patent application Ser. No. 469,889 filed May 14, 1974, now U.S. Pat. No. 3,961,048 there is described and claimed a water-soluble pharmaceutical complex comprising partricin and/or partricin methyl ester and at least one anionic and/or cationic surfactant. The only specific examples of such surfactants mentioned in U.S. Pat. No. 3,961,048 are sodium lauryl sulphate, sodium tetradecyl sulphate and benzalkonium chloride. However, the prolonged administration of the sulphate esters of higher alcohols is not always free from danger, particularly when they are injected by the intravenous route; sodium lauryl sulphate, for example, given in high doses and for prolonged endovenous treatments, can exert a toxic effect on the lungs, kidney and liver.

Continuing our investigations, we have now found that partricin and its alkyl esters can be rendered water-soluble by complex formation with sodium desoxycholate and/or sodium dehydrocholate.

SUMMARY OF THE INVENTION

Thus, according to the present invention, there is provided a water-soluble pharmaceutical complex, comprising an antibiotic selected from the group consisting of partricin and/or the alkyl esters thereof and a compound selected from the group consisting of sodium desoxycholate and/or sodium dehydrocholate.

DETAILED DESCRIPTION OF THE INVENTION

These new water-soluble complexes according to the present invention do not give rise to any special problems of toxicity, especially when it is borne in mind, for example, that sodium desoxycholate is already used in human liver therapy. The water-solubilisation of partricin and of its alkyl esters by complex formation with sodium desoxycholate and/or sodium dehydrocholate depends upon the physical form of the antibiotic; the best water-soluble complexes of the antibiotics in question are obtained by using the amorphous forms of the antibiotics rather than the crystalline forms. The antibiotics in the amorphous form can be obtained by dissolving them in an appropriate solvent, for example dimethyl sulphoxide, followed by precipitation with water. In the case of partricin, the solubility in water increases with increased pH value. Thus, for example, at pH 10 a concentration value of approximately 10,000 $\gamma$/ml. is obtained, whilst at a pH of 8 a concentration value of about 6,000 $\gamma$/ml. is achieved. In the case of the methyl ester of partricin, on the other hand, the concentration does not vary when the pH varies.

The new complexes according to the present invention can be prepared by dissolving partricin and/or at least one alkyl ester thereof in an aqueous suspension or solution containing sodium desoxycholate and/or sodium dehydrocholate, whereafter, if desired, the complex can be isolated therefrom, for example by lyophilisation.

Aqueous solutions containing partricin and/or an alkyl ester thereof in the form of complexes with sodium desoxycholate and/or sodium dehydrocholate can be subjected to sterile filtration and lyophilised; the yellow powder obtained in this way may be re-dissolved in sterile and pyrogen-free water and injected.

The complexes with which the present invention is concerned give, in alcoholic solution, an ultra-violet spectrum which is equal to that of the antibiotic alone, the same also applying to the results of thin layer chromatography.

The aqueous solutions of the new products are stable in a pH range of from 8 to 11, as has been demonstrated microbiologically. After 24 hours at ambient temperature, aqueous solutions containing 10,000 $\gamma$/ml. show a negligible degree of degradation.

The new complexes according to the present invention can be administered not only parenterally but also orally, rectally and vaginally. This solubilisation provides important advantages from the clinical point of view, in that the solubilised derivatives of partricin and of its alkyl esters can give therapeutically effective blood levels not only after parenteral administration but also after oral administration, which is particularly advantageous not only in the case of serious systemic mycotic infections but also, for example, in the case of trichomoniasis where the topical route may be used in association with the oral route, so that the protozoa are attacked from two directions.

Furthermore, in the case of topical administration, the water-solubilisation also renders the antibiotic more bio-available.

From the pharmacological point of view, the complexes have toxicities by the oral, intraperitoneal and endovenous routes which are no higher than those of the antibiotic contained therein.

The complexes described in the present invention have a micro-biological activity which may be superimposed on that of partricin and partricin methyl ester described in the U.S. Patents mentioned hereinbefore.

The following Examples are given for the purpose of illustrating the present invention:

EXAMPLE 1.

7.5 g. of particin are dissolved in 150 ml. of dimethyl sulphoxide. The solution is stirred at ambient temperature until dissolution is complete, whereafter the partricin is precipitated by the addition of 750 ml. of water containing 0.4% by weight of sodium chloride. The extremely fine precipitate thus obtained is filtered off with suction, thoroughly washed with water and suspended in 120 ml. of water.

A suspension is prepared of 7.5 g. of desoxycholic acid in 100 ml. of water. This is then adjusted to a pH of 9.5 by adding a 1N aqueous sodium hydroxide solution so as to give complete solution. The suspension of partricin is then added to the solution of sodium desoxycholate, stirred for 1 hour and filtered. The filtered solution contains 6000 U partricin/ml. and can be lyophilised.

EXAMPLE 2

5 g. of partricin are dissolved in 100 ml. of dimethyl sulphoxide. The solution is stirred at ambient temperature until dissolution is complete, whereafter the partricin is precipitated by the addition of 500 ml. of water containing 0.4% by weight of sodium chloride. An extremely fine precipitate is obtained which is filtered off with suction, thoroughly washed with water and suspended in 80 ml. of water.

This suspension is then added to a solution of 5 g. of desoxycholic acid in 70 ml. of water and adjusted to a pH of 9.5 with a 1 N aqueous sodium hydroxide solution. The pH is then adjusted to 10 with a 1 N aqueous sodium hydroxide solution, stirred for 1 hour at ambient temperature and filtered. The solution obtained, which contains 10,500 U of partricin/ml., is lyophilised.

EXAMPLE 3

12 g. of partricin methyl ester are dissolved in 240 ml. of dimethyl sulphoxide. The solution is stirred at ambient temperature until dissolution is complete, whereafter the ester is precipitated by the addition of 1200 ml. of water containing 0.4% by weight of sodium chloride. The precipiate obtained is filtered off, thoroughly washed with water and then suspended in 200 ml. of water. The extremely fine suspension thus obtained is added to a solution of 12 g. of desoxycholic acid in 170 ml. of water and adjusted to a pH of 9.5 by the addition of a 1 N aqueous sodium hydroxide solution. This solution is stirred for 2 hours at ambient temperature, filtered and the filtrate lyophilised. A yellow powder is obtained with an activity of 375 U partricin methyl ester/mg.

EXAMPLE 4

6 g. of partricin methyl ester are dissolved in 120 ml. of dimethyl sulphoxide. The solution is stirred at ambient temperature until dissolution is complete, whereafter the ester is precipitated by the addition of 600 ml. of water containing 0.4% by weight of sodium chloride. The precipitate obtained is filtered off, thoroughly washed with water and then suspended in 100 ml. of water, whereafter the suspension is poured into a solution of 6 g. of desoxycholic acid in 80 ml. of water adjusted to a pH of 9.5 with a 1 N aqueous sodium hydroxide solution. The resultant suspension is adjusted to a pH of 10 with a 1 N aqueous sodium hydroxide solution, stirred for 2 hours and then filtered. The filtrate is lyophilised to give a yellow powder having an activity of 350 U partricin methyl ester/mg.

EXAMPLE 5

3 g. of partricin are dissolved in 60 ml. of dimethyl sulphoxide. When the partricin is completely dissolved, the solution is poured into 300 ml. of water containing 0.4% by weight of sodium chloride. The precipitate obtained is filtered off, thoroughly washed with water and then suspended in 50 ml. of water. The suspension thus obtained is poured into 40 ml. of water containing 3 g. of dehydrocholic acid and adjusted to a pH of 9.4 with a 1 N aqueous sodium hydroxide solution. After stirring for 1 hour, the solution is filtered and lyophilised.

EXAMPLE 6

5 g. of partricin are dissolved in 100 ml. of dimethyl sulphoxide. When dissolution is complete, the solution is poured into 500 ml. of water containing 0.4% by weight of sodium chloride. The precipitate obtained is filtered off, thoroughly washed with water and the precipitate suspended in 80 ml. of water.

5 g. of dehydrocholic acid are dissolved in 70 ml. of water by adjusting the pH to 9.4 by the addition of a 1 N aqueous sodium hydroxide solution. The extremely fine aqueous suspension of partricin is then added thereto, whereafter the pH is adjusted to 10 by the addition of a 1 N aqueous sodium hydroxide solution. After stirring for 1 hour, the solution is filtered and lyophilised.

EXAMPLE 7

2 g. of partricin methyl ester are dissolved in 40 ml. of dimethyl sulphoxide. When dissolution is complete, the ester is precipitated by the addition of 200 ml. of water containing 0.4% by weight of sodium chloride; the precipitate is filtered off, thoroughly washed with water and the precipitate suspended in 30 ml. of water. This suspension is then poured into 30 ml. of water containing 2 g. of dehydrocholic acid and adjusted to a pH of 9.4 by the addition of a 1 N aqueous sodium hydroxide solution. After stirring for 2 hours, the solution is filtered and lyophilised.

EXAMPLE 8

2 g. of partricin ethyl ester are dissolved in 40 ml. of dimethyl sulphoxide. The ester is then precipitated by the addition of 200 ml. of water containing 0.4% by weight of sodium chloride. The precipitate is filtered off, washed with water and the precipitate suspended in 30 ml. of water, whereafter the suspension is added to a solution of 2 g. of desoxycholic acid in 30 ml. of water with a pH of 9.5. After stirring for 1 hour at ambient temperature, the solution is filtered and lyophilised.

The complexes according to the present invention can be admixed with solid or liquid pharmaceutical diluents or carriers. They can be administered orally in the form of tablets, capsules, dragees, spersoids or the like, containing, in the case of the complexes of partricin, up to 2 mg. of active material and, in the case of methyl partricin, 25 mg. or more of active material.

For topical use, there can be used, for example, linaments, lotions, sprays, creams, ointments or the like containing up to 0.06% by weight of complex.

Vaginal tablets and pessaries and rectal suppositories can contain up to 10 mg. by weight of complex, mixed with suitable excipients.

For intramuscular use, the products can be employed in a concentration of, for example, 1% by weight.

For slow endovenous administration, a complex containing partricin methyl ester can be used in a concentration of 0.2 to 0.5 mg./ml. in sterile water or in a 5% solution of dextrose or the like.

Solid compositions for oral, rectal or vaginal administration include compressed tablets, effervescent tablets, pills, dispersible powders, capsules, granules and suppositories. In such solid compositions, the active material complex is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvents, such as wetting and suspension agents and sweetening and flavouring agents.

The compositions and according to the present invention, for oral administration, include capsules of absorbable material, such as gelatine, containing the active material, with or without the addition of diluents or excipients.

Preparations according to the present invention for parenteral administration include sterile aqueous or non-aqueous solutions, suspensions or emulsions. Examples of non-aqueous solvents or suspending media include propylene glycol, polyethylene glycol, vegetable oils, such as olive oil, and injectable organic esters, such as ethyl oleate. These compositions may also contain adjuvants, such as wetting, emulsifying and dispersing agents. They may be sterilized, for example, by filtration through bacteria-retaining filters, by incorporation into the compositions of sterilising agents, by irradiation or by heating. They may also be produced in the form of sterile solid compositions, which can be dissolved in sterile water or some other sterile injectable medium immediately before use.

The percentage of active complex in the compositions of the present invention may be varied, it being necessary that it should constitute a proportion such that a suitable dosage for the desired therapeutic effect shall be obtained. In the case of dosage units for oral administration, each unit can contain up to 2 g. of partricin or up to 3 g. of partricin methyl ester. In the case of compositions for topical, vaginal or rectal administration, the content of complex can be up to about 0.06% by weight.

Examples of pharmaceutical compositions containing the polyene antibiotic include the following:

Example 9.
Ointment
    Composition:

| | | |
|---|---|---|
| the product of Example 1 | 0.1 | g. |
| alcoholic fats | 60 | g. |
| lanolin | 15 | g. |
| polyethylene glycol 1540 monostearate | ad 100 | g. |

Example 10.
Liniment
    Composition:

| | | |
|---|---|---|
| the product of Example 3 | 0.1 | g. |
| dimethylacetamide | 5 | g. |
| anhydrous lanolin | 15 | g. |
| cetyl alcohol | 30 | g. |
| oleyl alcohol | 15 | g. |
| sorbitan trioleate | 10 | g. |
| polyethylene glycol 1540 monostearate | 24 | g. |

Example 11.
Vaginal suppositories.
    Each vaginal suppository contains:

| | | |
|---|---|---|
| the product of Example 7 | 5 | mg. |
| dimethyl acetamide | 50 | mg. |
| polyethylene glycol 1540 monostearate | 1.35 | g. |
| cetyl alcohol | 0.500 | g. |

Example 12.
Vaginal suppositories.
    Each vaginal suppository contains:

| | | |
|---|---|---|
| the product of Example 1 | 10 | mg. |
| dimethyl acetamide | 50 | mg. |
| polyethylene glycol 1540 monostearate | 1.35 | g. |
| cetyl alcohol | 0.500 | g. |

The pharmaceutical compositions illustrated in Examples 9 to 12 above show valuable anti-fungal and anti-protozoal activity when administered to humans.

We claim:
1. A water-soluble pharmaceutical complex, comprising an antibiotic selected from the group consisting of partricin, partricin methyl ester and partricin ethyl ester and a complex-forming compound selected from the group consisting of sodium desoxycholate and sodium dehydrocholate, wherein the weight ratio of the antibiotic to the complex-forming compound is about 1:1, said partricin having an Rf value of about 0.50 on silica gel using butanol-ethanol-acetone-25% ammonium hydroxide in a ratio of 2:5:1:3 as eluent, ultraviolet absorption maxima at 410, 379, 359 and 341 m$\mu$ in ethanol at a concentration of about 0.01 mg/ml, infrared absorption maxima at 3355, 1704, 1596, 1175, 1070, 995 and 850 cm$^{-1}$ in nujol, and an elemental analysis of C = 62.8%, H = 7.9%, N= 3.2% and O =25.2% said complex having an ultraviolet absorption spectrum and Rf value equal to the ultraviolet absorption spectrum and Rf value of the antibiotic alone.

2. A complex according to claim 1, wherein the antibiotic is the partricin methyl ester.

3. A complex according to claim 1, wherein the antibiotic is the partricin ethyl ester.

4. A pharmaceutical composition, comprising a complex according to claim 1, in admixture with a member selected from the group consisting of solid and liquid pharmaceutical diluents and carriers.

* * * * *